United States Patent [19]

Connolly

[11] 4,015,617
[45] Apr. 5, 1977

[54] ANALGESIC APPARATUS

[75] Inventor: Edward A. Connolly, Williamsville, N.Y.

[73] Assignee: Fraser Sweatman, Inc., Lancaster, N.Y.

[22] Filed: Mar. 25, 1975

[21] Appl. No.: 561,906

[52] U.S. Cl. .............................. 137/88; 137/605
[51] Int. Cl.$^2$ ...................................... G05D 11/03
[58] Field of Search ....... 137/88, 606, 111, 101.19, 137/605; 73/209, 207, 208, 210

[56] References Cited
UNITED STATES PATENTS

| | | | |
|---|---|---|---|
| 2,643,944 | 6/1953 | Malir, Jr. .................. | 137/111 X |
| 3,302,053 | 5/1962 | Ross et al. .................. | 137/111 |
| 3,534,753 | 10/1970 | Ollivier .................. | 137/88 X |
| 3,582,662 | 6/1971 | Soika .................. | 73/209 X |
| 3,677,296 | 7/1972 | Berger .................. | 137/606 |
| 3,739,799 | 6/1973 | Bickford .................. | 137/88 |
| 3,809,109 | 5/1974 | Breiling .................. | 137/88 |

*Primary Examiner*—William R. Cline
*Attorney, Agent, or Firm*—Christel & Bean

[57] ABSTRACT

A gas flow control system including a control for varying the flow rate of only one of two gaseous components forming an analgesic mixture to selectively vary the relative proportions thereof up to a pre-established maximum concentration of the one component and a control to vary the total flow rate of these components without varying the relative proportions thereof. Flow meters are provided to measure the relative flow rates and thereby determine the concentration of the gaseous components.

8 Claims, 2 Drawing Figures

ANALGESIC APPARATUS

BACKGROUND OF THE INVENTION

This invention relates generally to an analgesic apparatus and, more particularly, to a gas flow control system for analgesic apparatus of the continuous flow type.

Continuous flow type analgesic machines are widely used today in conjunction with a breathing circuit to provide a complete analgesic system. These machines blend or mix a gaseous analgesic with oxygen in proportional amounts to produce a gaseous mixture having a desired analgesic concentration. Conventionally, such machines utilize individual control valves associated with individual flow meters to separately control the flow of each gas in order to obtain the desired oxygen concentration at the required total flow rate. Such arrangements sometimes provide a minimum oxygen flow at all times and a maximum flow of analgesic gas to ensure a minimum dilution of the analgesic gas. When it becomes necessary to either adjust the oxygen concentration while maintaining the total flow rate constant or adjust the total flow rate without varying the oxygen concentration each of the control valves must be adjusted and a computation performed to determine the flow rate required of each gaseous component to maintain the desired total flow rate. It also is known to provide a control for varying the flow rates of both components without varying the total flow rate. It is desirable to be able to limit the relative proportions of the components without requiring a minimum flow of oxygen and a maximum flow of analgesic gas while permitting the adjustment of the total flow rate without varying the relative proportions previously selected.

SUMMARY OF THE INVENTION

Accordingly, it is an object of the present invention to provide a continuous flow analgesic apparatus having means to selectively vary the proportions of the gaseous components up to a preselected maximum ratio by controlling the flow of only one of the gaseous components.

It is a further object of the present invention to provide the foregoing control system with means for varying the total flow rate of the gaseous components without affecting the relative proportions thereof.

Another object is to provide a means to limit the relative proportions of the gaseous components without requiring a minimum flow control of oxygen and a maximum flow control of analgesic gas.

The analgesic apparatus of the present invention is characterized by the provision of a gas flow control system incorporating means for limiting the maximum concentration of one gaseous component and a single manually operable control for varying the flow of such one component relative to the fixed flow of another gaseous component to selectively vary the relative proportions of the two gaseous components up to a maximum ratio. Flow meters indicate the respective flow rates of the gaseous components to verify the accurary of the selected proportions. Another control is operable to vary the total flow rate of these components without affecting the relative proportions thereof.

These and other objects, advantages and characterizing features of the present invention will become clearly apparent from the ensuing detailed description of an illustrative embodiment thereof, taken together with the accompanying drawings wherein like reference numerals denote like parts throughout.

BRIEF DESCRIPTION OF THE DRAWING FIGURES

FIG. 1 is a front elevational view of one form of a continuous flow analgesic apparatus incorporating the gas flow control system of this invention; and FIG. 2 is a schematic view of the gas flow control system of the present invention.

DETAILED DESCRIPTION OF AN ILLUSTRATIVE EMBODIMENT

Figure 1:
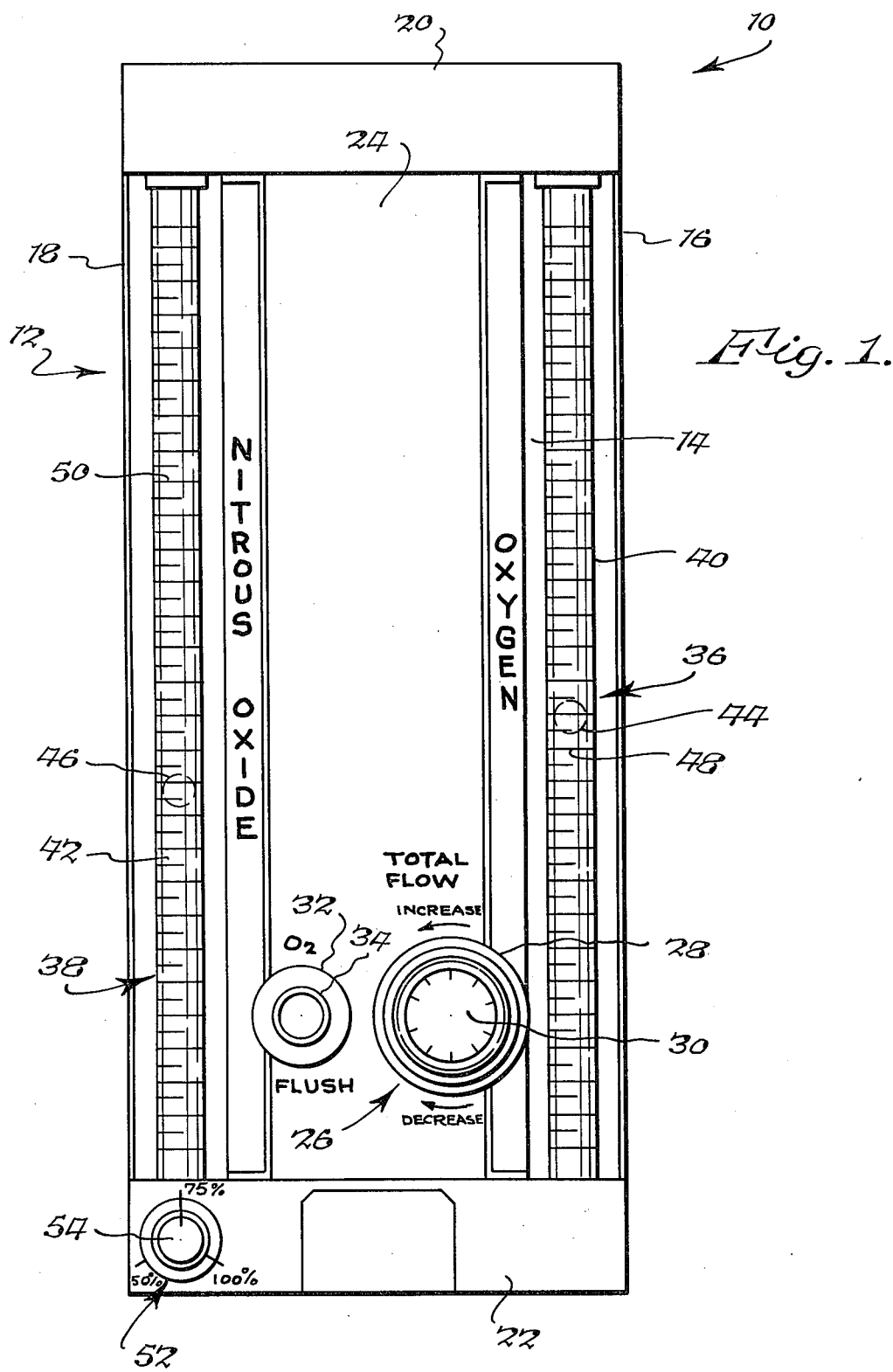

Referring now in detail to the illustrative embodiment depicted in the accompanying drawings, there is shown in FIG. 1 a continuous flow analgesic apparatus, generally designated 10, constructed in accordance with this invention, comprising a housing 12 of a generally rectangular, box-like construction for mounting various elements, including the improved gas flow control system of this invention, in a self-contained unit. Housing 12 includes a front panel 14 formed of plexiglass or any other suitable transparent material, a rear panel (not shown), a pair of side members 16 and 18 connecting the front and rear panels together, an upper manifold 20 and a lower manifold 22 forming the top and bottom structural members, respectively, of housing 12.

A decal strip 24 is secured centrally on front panel 14 and is provided with various legends and indicia imprinted thereon bearing information to aid the anesthetist in operating and monitoring apparatus 10. Projecting outwardly from the lower right portion of front panel 14 is a total flow control valve or regulator, generally designated 26, having a casing 28 and a manually operable regulating knob 30 at the forward end of casing 28. A flush valve 32 also is mounted on housing 12 and projects outwardly from the lower left portion of front panel 14 in laterally spaced relation to total flow control valve 26. Valve 32 is provided with a manually operable knob 34 in close proximity to regulating knob 30 for convenient accessibility to the user thereof.

A pair of flow meters 36 and 38 are mounted in housing 12 between the front and rear panels thereof on opposite sides of decal strip 24 for measuring and visually indicating the flow of oxygen gas and a gaseous analgesic, such as nitrous oxide for example, respectively. These flow meters 36 and 38 are conventional and comprise the usual vertically extending, transparent tapered tubes 40 and 42 having balls 44 and 46 therein which have specific gravities greater than the specific gravities of the gases being measured, respectively. The stream of gas flowing between each ball and the inner surface of its respective tube produces a drag force on the ball which rises until it reaches static position of equilibrium in the tube. As the flow rate varies, the position of the ball in the tube varies accordingly so that the position of the ball in the tube indicates a particular flow rate. Suitable calibrated scales 48 and 50 are inscribed on tubes 40 and 42 to indicate the rate of flow of the respective gases as measured by balls 44 and 46 within their associated tubes.

A needle valve 52 is mounted in the lower manifold 20 and is provided with a stem (not shown) having a manually operable handle or knob 54 projecting outwardly from lower manifold 20 adjacent the left end thereof, as viewed in FIG. 1, for convenient accessibility to the user. Needle valve 52 controls the flow of the gaseous analgesic and thereby the concentration thereof in the gaseous mixture, as will hereinafter be more fully described in connection with the operation of the gas flow control system.

Figure 2:
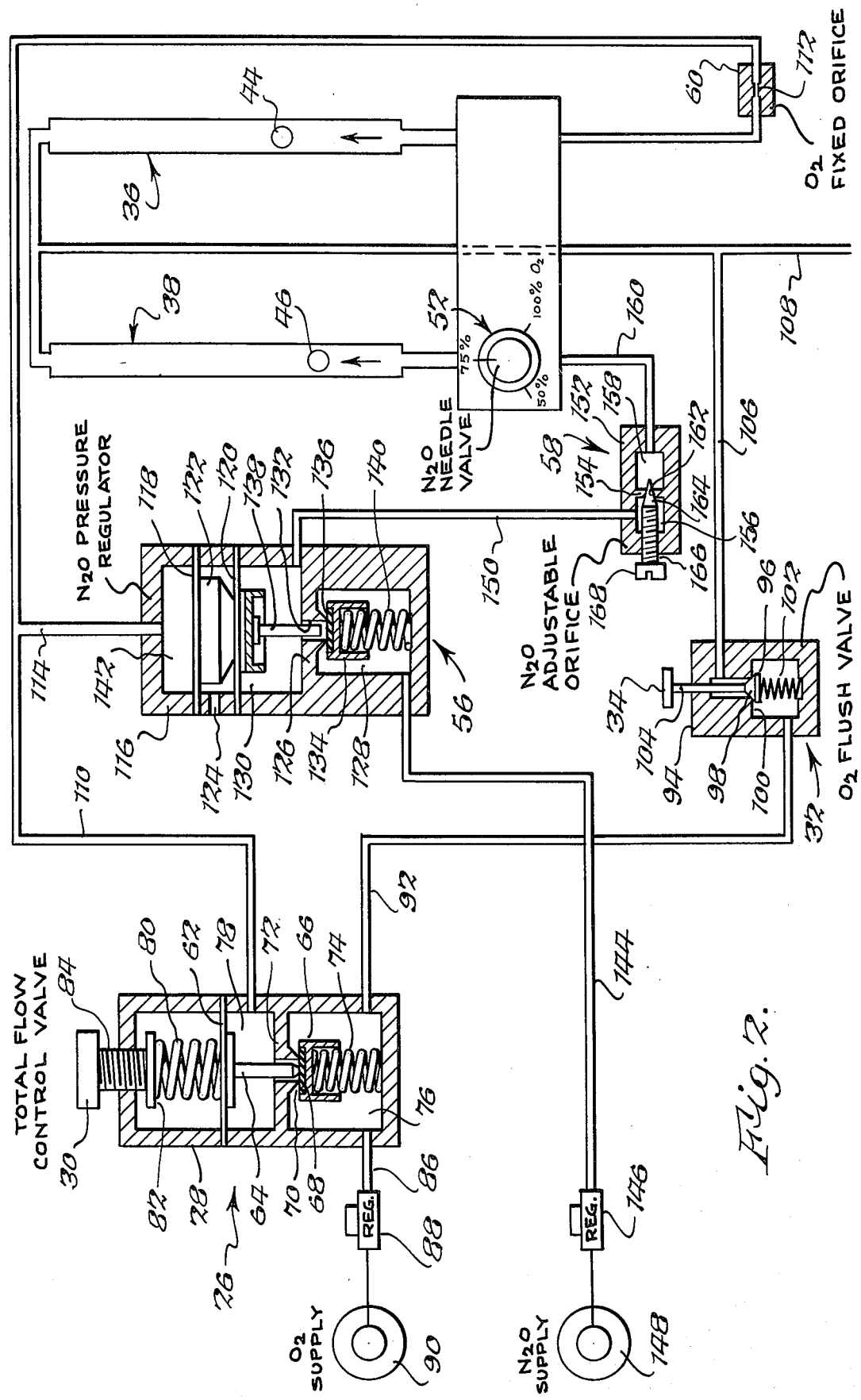

The gas flow control system, which can be physically mounted in housing 12, is shown schematically in FIG. 2. In the illustrative embodiment of this invention, the gas flow control system is used in an analgesic procedure for blending or mixing a gaseous analgesic, such as nitrous oxide for example, with oxygen. The illustrative control system includes total flow control valve 26, flush valve 32, a fail-safe nitrous oxide regulator 56, an adjustable orifice valve 58 on the nitrous oxide side, needle valve 52, a fixed orifice 60 on the oxygen side, and flow meters 36 and 38.

Total flow rate control valve 26 comprises a diaphragm 62 mounted in casing 28 and engaging against a plunger or stem 64, which can be rigidly secured thereto, for movement along with diaphragm 62. Stem 64 is engagable with a cup-shaped valve 66 having a resiliently yieldable seating surface 68 adapted to engage a valve seat 70 formed on a partition 72 in casing 28. Valve 66 is biased toward seat 70 by means of a helical compression spring 74. Partition 72 separates casing 28 into a pressure inlet chamber 76 and a control pressure chamber 78, defined between partition 72 and diaphgram 62. A compression spring 80 is positioned between diaphragm 62 and an abutment surface 82 formed on the end of a threaded shank 84 which carries knob 30. Threading shank 84 inwardly increases the force of spring 80 against diaphragm 62 to move stem 64 inwardly, unseating valve 66 against the bias of spring 74 to increase the pressure in control chamber 78. Threading shank 84 in the opposite direction permits valve 66 to close under the influence of spring 74, to decrease the pressure in chamber 78. The inlet of pressure chamber 76 is connected by a supply conduit 86 through a pressure regulator 88 to a suitable source of oxygen under pressure, such as a pressurized oxygen tank 90, for example.

The outlet of inlet pressure chamber 76 is connected to flush valve 32 by means of a conduit 92. As shown schematically in FIG. 2, flush valve 32 comprises a casing 94 in which is mounted a poppet type valve 96 having a seating surface 98 biased into engagement with a valve seat 100 by a compression spring 102 for maintaining the valve normally closed. Valve 96 is provided with a stem 104 connected to knob 34 for actuation thereby. The outlet valve 32 is connected by a conduit 106 to a common outlet 108 from the flowmeters leading to the breathing circuit. When necessary or desired, knob 34 is actuated to unseat valve 96 for purging or flushing the breathing circuit with oxygen and rapidly inflating the typical flexible reservoir bag (not shown) conventionally tapped into the common outlet 108, as is well known.

The outlet of pressure control chamber 78 is connected directly to oxygen flow meter 36 by means of a conduit 110. Fixed orifice 60 is located in conduit 110 just upstream of flow meter 36 and is provided with a restricted passage 112 to establish a fixed flow rate of oxygen passing through flow meter 36 and ultimately into common outlet 108. Thus, a maximum rate of oxygen flow is determined by fixed orifice 60.

The outlet of pressure control chamber 78 also is connected to the nitrous oxide regulator 56 by means of a conduit 114 tapped into the oxygen delivery conduit 110. Regulator 56 comprises a housing 116 in which is mounted a pair of spaced diaphragms 118 and 120 operating as a unit and spaced apart by a spacer member 122. The space between diaphragms 118 and 120 is vented as at 124. A partition 126 is provided in housing 116 for defining an inlet chamber 128 and an outlet chamber 130 and is provided with a passage 132 establishing communication between chambers 128 and 130. A cup-shaped valve 134, having a seating surface 186, controls the opening and closing of passage 132. A plunger 138, rigidly secured to diaphragm 120, is movable through passage 132 and engagable with valve 134 for unseating the latter against the bias of a compression spring 140 upon downward movement of diaphragm 120. A control chamber 142 is defined between diaphragm 118 and the upper end of housing 116 and reflects the pressure of the oxygen gas established in pressure control chamber 78 of total flow control valve 26, as determined by the setting of knob 30.

Inlet chamber 128 of nitrous oxide regulator 56 is connected by a supply conduit 144 through a pressure regulator 146 to a suitable source of nitrous oxide under pressure, such as a pressurized nitrous oxide tank 148, for example. Outlet chamber 130 of regulator 56 is connected to adjustable orifice valve 58 by a conduit 150.

Valve 58 comprises a body 152 provided with a partition 154 defining inlet and outlet chambers 156 and 158 communicating with conduit 150 and a conduit 160, respectively, the latter leading to flow meter 38. An orifice 162, formed in partition 154, establishes communication between chambers 156 and 158. A metering valve 164 is located in orifice 162 for varying the size thereof. Metering valve 164 is provided with a threaded stem 166 having a slotted head 168 on the outer end thereof for receiving an appropriate tool. Threading stem 166 in either direction moves metering valve 164 inwardly or outwardly of orifice 162 to vary the size thereof and thereby the rate of flow of nitrous oxide therethrough. The setting of valve 58 determines the maximum nitrous oxide flow rate and consequently the maximum concentration of nitrous oxide in the analgesic-oxygen mixture. It is intended that the position of valve 58 be pre-set at the factory rather than operator or attendant adjusted, for safety reasons. Since it has been found that a 50% nitrous oxide concentration adequately sedates substantially all patients, valve 58 preferably is adjusted to deliver the same maximum flow rate as the fixed oxygen orifice 60 in order to obtain a maximum 50% nitrous oxide concentration.

It should be appreciated that nitrous oxide concentration of less than this maximum 50% level will suffice in most applications. To this end, needle valve 52, which is interposed between valve 58 and flow meter 38 for controlling the flow of nitrous oxide in conduit 160 downstream of valve 58, is operative to reduce the nitrous oxide concentration below the maximum concentration dictated by valve 58, as required in a specific application.

In operation, needle valve 52 is adjusted to admit the desired concentration or percentage of nitrous oxide into the breathing circuit. Assuming that a 50% concentration is desired, needle valve 52 is set to the fully opened position allowing maximum flow of nitrous oxide through conduit 160, as dictated by the factory setting of valve 58 which, in the instant example, is adjusted to the same flow rate as fixed oxygen orifice 60. Total flow control valve knob 30 is turned to establish the desired total flow rate. Turning knob 30 loads spring 80 to deflect diaphragm 62, carrying stem 64 with it and consequently unseating valve 66.

Oxygen gas is supplied to conduit 86 under a predetermined pressure, as dictated by regulator 88 and gaseous nitrous oxide is supplied to conduit 144 under a predetermined pressure, as determined by regulator 146. Oxygen gas flows into chamber 76, past the unseated valve 66, into chamber 78 and outwardly into conduit 110. When oxygen pressure in chamber 78 acting against the spring loaded diaphragm 62 produces a force, just slightly greater than the force of spring 80, diaphragm 62 is caused to flex against the bias of spring 80, carrying with it stem 64 and allowing valve 66 to seat by means of spring 74, thereby regulating the oxygen pressure in chamber 78 as determined by the setting of valve 26. Oxygen gas under this regulated pressure flows via conduit 110 at a rate controlled by fixed orifice 60 and visually verified by flow meter 36 into the outlet conduit 108 leading to the breathing circuit.

The pressure of the oxygen gas in conduit 110 also is reflected in control chamber 142 of nitrous oxide pressure regulator 56 and acts against diaphragm 118 to move plunger 138 against valve 134 to unseat the latter against the bias of spring 140 and admit gaseous nitrous oxide from chamber 128 into chamber 130 via passage 132. When the nitrous oxide pressure acting in chamber 130 begins to exceed the oxygen control pressure in chamber 142, diaphragms 120 and 118 will be flexed as a unit allowing valve 134 to seat under the influence of spring 140, thereby regulating the pressure of nitrous oxide gas in chamber 130. Thus, the pressure of the nitrous oxide gas in chamber 130 is maintained equal to the pressure of the oxygen gas. Nitrous oxide under this controlled pressure flows via conduit 150 at a rate controlled by pre-set orifice valve 58 and needle valve 52, which ever has the lower setting, and visually verified by flow meter 38, into outlet conduit 108 leading to the breathing circuit. Since the oxygen gas serves as the control pressure fluid in regulator 56, failure or depletion of the oxygen supply will cause the nitrous oxide regulator 56 to shut off automatically and thereby prevent the possibility of an overdosage of nitrous oxide into the breathing circuit.

The total flow rate introduced into line 108 and the breathing circuit can be varied at any time during the analgesic procedure simply by rotating knob 30 in either direction to obtain the desired total flow rate without in any way affecting the proportions of the gaseous components. When it is desired to lower the proportion or the concentration of nitrous oxide in the mixture below the 50% level determined by the setting of valve 58, a needle valve 52 is rotated in a direction to further restrict the rate of flow of nitrous oxide into the system and thereby provide the desired reduced proportion. Assuming that by way of example, that only a 25% concentration of nitrous oxide is desired in the mixture, needle valve 52 is turned to provide a restriction in conduit 160 approximately one-third the size of fixed orifice 60 to obtain a mixture having a ratio of one to three. Flow meter 38 is observed and compared to flow meter 36 to visually verify the relative rates of flow of the two components and the accuracy of the setting of valve 52 to produce a mixture of the desired proportions.

From the foregoing, it is apparent that the objects of the present invention have been fully accomplished. An improved gas flow control system for a continuous flow analgesic apparatus is provided for selectively varying the relative proportions of the gaseous components up to a pre-selected maximum concentration of the analgesic component, as established by a factor pre-set adjustable orifice, by the manipulation of a single control proportioning the flow rate of the analgesic component relative to the fixed flow rate of the other, oxygen component. The individual flow meters provide visual verification of the selected relative proportions of the gaseous components. Also, the system includes a control for selectively varying the total flow rate of the gaseous components without varying the relative proportions thereof. In addition, a number of safety features are incorporated in the gas flow control system of the present invention, including the utilization of the oxygen component as the control pressure for activating the nitrous oxide pressure regulator. Should the oxygen supply fail, the nitrous oxide regulator is automatically disabled to prevent overdosage of nitrous oxide into the breathing circuit. The double diaphragm arrangement of the nitrous oxide regulator insures against the uncontrolled mixing of the two gases in the event of leakage of one of such diaphragms. The factory adjustable orifice incorporated in the nitrous oxide line limits the maximum concentration of nitrous oxide admitted into the breathing circuit, while the needle valve located downstream of the adjustable orifice enables the concentration of nitrous oxide to be selectively varied to provide any desired proportion up to this maximum concentration.

It should be understood that the gas flow control system of this invention is not limited in use with gaseous analgesic components, but has utility in any application where it is desired to blend two gases in selected proportions at desired flow rates.

An embodiment of this invention having been described and illustrated in detail, it is to be understood that this has been done by way of illustration only.

I claim:

1. Analgesic apparatus comprising at least two flowmeters; means for supplying one fluid component to one of said flowmeters; means for supplying a second fluid component to another of said flowmeters; fixed orifice means having a permanently restricted passage for determining the maximum rate of flow of said one component; pre-setting means for determining the maximum rate of flow of said second component thereby to establish maximum relative proportions of said components entering said flowmeters, the position of said pre-setting means being set prior to normal use of said apparatus so as to eliminate the necessity for any adjustment thereof during normal use of said apparatus; control means for varying the rate of flow of said second component independently of the rate of flow of said one component during use of said apparatus in order to selectively vary the relative proportions of said components up to said maximum relative proportions and flow control means operable to selectively vary the total rate of flow of said fluid components substantially without varying the relative proportion thereof.

2. Analgesic apparatus according to claim 1 wherein said flow control means comprises a fluid regulator having a fluid inlet connected to a source of said one fluid component under pressure and a fluid outlet connected to said one flowmeter; valve means in said fluid regulator for controlling the flow of said one fluid component from said fluid inlet to said fluid outlet; and adjustable spring biased means for actuating said valve means to extablish communication between said fluid inlet and said fluid outlet.

3. Analgesic apparatus according to claim 2, together with a second fluid regulator having a fluid inlet connected to a source of said second fluid component under pressure and a fluid outlet connected to said other flowmeter; valve means in said second fluid regulator for controlling the flow of said second fluid component from said fluid inlet to said fluid outlet; a control chamber in said second fluid regulator; conduit means connecting said control chamber to said first fluid regulator outlet for establishing a control pressure in said chamber; and means responsive to pressure in said control chamber as determined by operation of said first regulator for actuating said second regulator valve means.

4. Analgesic apparatus according to claim 3 wherein said responsive means in said second fluid regulator comprises a pair of spaced diaphragms connected together and interposed between said fluid outlet and said control chamber of said second fluid regulator; and means for venting the space between said pair of diaphragms to the ambient atmosphere.

5. Analgesic apparatus according to claim 1 wherein said pre-setting means comprises an orifice valve means adjustable for effecting a desired maximum rate of flow of said second component relative to said maximum rate of flow of said one fluid component to establish the maximum concentration of said second fluid component in the resulting mixture of the two fluid components.

6. Analgesic apparatus according to claim 5 wherein said control means comprises a valve means operable only on said second component for varying the concentration of said second fluid component below the level of said maximum concentration.

7. Analgesic apparatus according to claim 6 wherein said control means further includes indicia for showing in a calibrated manner the relative percent concentration of said fluid components.

8. Analgesic apparatus as set forth in claim 1, wherein said first component is oxygen and said second component is an analgesic gas.

* * * * *

UNITED STATES PATENT AND TRADEMARK OFFICE
CERTIFICATE OF CORRECTION

PATENT NO. : 4,015,617
DATED : April 5, 1977
INVENTOR(S) : Edward A. Connolly

It is certified that error appears in the above-identified patent and that said Letters Patent are hereby corrected as shown below:

Claim 1, column 6, line 58, insert --normal-- after "during".

Signed and Sealed this

Thirteenth Day of September 1977

[SEAL]

Attest:

RUTH C. MASON
Attesting Officer

LUTRELLE F. PARKER
Acting Commissioner of Patents and Trademarks